United States Patent
Hagen et al.

(10) Patent No.: US 6,572,636 B1
(45) Date of Patent: Jun. 3, 2003

(54) PULSE SENSING PATCH AND ASSOCIATED METHODS

(76) Inventors: Robert Sean Hagen, 413 S. Lakemont Ave., Winter Park, FL (US) 32792; Monty Montgomery, 2052 Butler Way, NW., Atlanta, GA (US) 30318

( * ) Notice: Subject to any disclaimer, the term of this patent is extended or adjusted under 35 U.S.C. 154(b) by 54 days.

(21) Appl. No.: 09/665,630

(22) Filed: Sep. 19, 2000

(51) Int. Cl.$^7$ ................................................ A61B 5/00
(52) U.S. Cl. ........................ 606/500; 600/485; 600/479
(58) Field of Search ........................ 600/485, 500–503, 600/476–480

(56) References Cited

U.S. PATENT DOCUMENTS

| | | | |
|---|---|---|---|
| 3,361,128 A | 1/1968 | Coleman | 128/2.05 |
| 3,602,213 A | 8/1971 | Howell | 128/2.05 F |
| 3,851,320 A | 11/1974 | Dahl | 340/189 M |
| 3,943,918 A | 3/1976 | Lewis | 128/2.1 A |
| 4,163,447 A * | 8/1979 | Orr | 600/503 |
| 4,258,719 A * | 3/1981 | Lewyn | 600/503 |
| 4,281,663 A | 8/1981 | Pringle | 128/689 |
| 4,305,401 A | 12/1981 | Reissmueller | 128/690 |
| 4,367,752 A | 1/1983 | Jimenez | 128/689 |
| 4,489,731 A | 12/1984 | Baumberg | 128/690 |
| 4,775,840 A | 10/1988 | Ohmori | 328/111 |
| 4,809,705 A | 3/1989 | Ascher | 128/710 |
| 4,867,170 A * | 9/1989 | Takahashi | 600/500 |
| 5,025,792 A * | 6/1991 | Hon et al. | 600/500 |
| 5,190,047 A | 3/1993 | Odagiri | 128/687 |
| 5,215,097 A | 6/1993 | Watabe | 128/689 |
| 5,228,449 A * | 7/1993 | Christ et al. | 600/500 |
| 5,406,952 A * | 4/1995 | Barnes et al. | 600/485 |
| 5,443,072 A | 8/1995 | Kagan | 128/691 |
| 5,483,967 A | 1/1996 | Ohtake | 128/695 |
| 5,586,555 A * | 12/1996 | Bobo, Jr. et al. | 600/500 |
| 5,670,944 A | 9/1997 | Myllymaki | 340/573 |
| 5,766,132 A * | 6/1998 | Yasukawa et al. | 600/503 |
| 5,783,997 A | 7/1998 | Saitoh et al. | 340/576 |
| 5,876,346 A * | 3/1999 | Corso | 600/500 |
| 5,876,350 A | 3/1999 | Lo | 600/519 |
| 5,906,582 A | 5/1999 | Kondo | 600/500 |
| 6,081,194 A * | 6/2000 | Sanchez | 600/503 |
| 6,277,079 B1 * | 8/2001 | Avicola et al. | 600/502 |

* cited by examiner

Primary Examiner—Robert L. Nasser
(74) Attorney, Agent, or Firm—Bracewell & Patterson LLP

(57) ABSTRACT

A pulse sensing patch and methods of forming and using the same are provided. The patch preferably includes a main body having an upper surface, a lower adhesive surface and an opening positioned in a medial portion of the main body. The pulse sensing patch also includes a housing having upper and lower portions positioned to surround the opening in the medial portion of the main body. The patch further includes a pulse sensor positioned within the housing for sensing a pulse, and a visual indicator positioned to overlie the pulse sensor within the housing for displaying a visually recognizable pattern of the pulse. The method of forming the medical pulse sensing patch includes forming an opening in the medial portion of the main body, positioning pulse sensor for sensing a pulse within the opening of the main body, and positioning a housing having upper and lower portions to surround the pulse sensor. The method of using the pulse sensing patch preferably includes removing the pulse sensing patch from a sterile package, positioning the pulse sensing patch to overlie a user's skin, activating the pulse sensing patch by removing a lubricant cover positioned adjacent a lower surface of the medical pulse sensing patch, and visualizing a predetermined indication pattern representing the pulse.

40 Claims, 5 Drawing Sheets

PULSE SENSING PATCH AND ASSOCIATED METHODS

FIELD OF THE INVENTION

The present invention relates to the health care, novelty, education and jewelry industries and, more particularly, to the field of medical pulse detection devices and methods of detecting and monitoring pulses.

BACKGROUND OF THE INVENTION

Medical device manufacturers have often tried to manufacture a device for sensing a pulse that is easy to use, simple to manufacture and small in size. Most current medical pulse sensing devices, however, are large in size, and difficult to operate. For example, U.S. Pat. No. 3,602,213, by Howell, titled *"Apparatus For Photoelctric Dermachromography,"* describes an apparatus for sensing blood flow under skin. A portion of the apparatus is adhesively attached to the skin, but is connected by leads or wires to a large power supply that provides the adhesively connected portion with power. This apparatus is also very bulky, is not readily disposable, and needs extensive medical training to install and use.

Manufacturers of pulse sensing devices also struggle with the problem of durability of the pulse sensing device. For example, U.S. Pat. No. 5,443,072, by Kagen, titled *"Miniature Disposable Blood Flow Monitor"* describes a monitor that adhesively attaches to skin. The blood flow monitor provides different colored indicators for different conditions of blood flow. This monitor, however, uses an exposed transducer to detect the blood flow. An exposed transducer often rapidly deteriorates when exposed to contaminating elements. This monitor is also difficult to use because it does not allow for a user to move the monitor along the skin until a pulse is located. The monitor is adhesively attached and detached from the skin until the pulse is located.

SUMMARY OF THE INVENTION

With the foregoing in mind, the present invention advantageously provides a pulse sensing patch and methods of forming and using the same. The pulse sensing patch allows caregivers to provide higher levels of care to patients by providing a fast and easy way to monitor a pulse. The pulse is a key component of hemodynamic monitoring. The medical pulse sensing patch advantageously eases the task of hemodynamic monitoring and insures adequate oxygenation and tissue perfusion. The medical pulse sensing patch may also advantageously be used as a children's educational toy or jewelry. The pulse sensing patch, for example, allows easy and safe use for children to learn the significance of blood flow within their own bodies.

More particularly, the present invention preferably includes a pulse sensing patch having a main body with an upper surface, a lower adhesive surface and an opening positioned in a medial portion of the main body. The pulse sensing patch also includes a housing having upper and lower portions positioned to surround the opening in the medial portion of the main body. The upper portion is positioned to contact the upper surface of the main body, and the lower portion is positioned to contact the lower surface of the main body. The pulse sensing patch still further includes pulse sensing means positioned within the housing for sensing a pulse. The pulse sensing patch also includes a plurality of visual indicators positioned in communication with the pulse sensing means and also positioned within the housing for displaying a visually recognizable pattern of the pulse. The medical pulse sensing patch also includes a lubricant positioned adjacent the lower surface of the medical pulse sensing patch and pulse patch activating means for activating the medical pulse sensing patch. The lubricant advantageously allows a user to move the patch along the skin to thereby locate a stronger pulse, before an adhesive connection between the patch and the skin is made.

The medical pulse sensing patch is advantageously cost effective to manufacture and distribute. The housing on the medical pulse sensing patch advantageously provides a seal to protect inner components of the medical pulse sensing patch from elements that cause rapid deterioration. The lubricant is advantageous because it allows a caregiver to apply the medical pulse sensing patch to the user and maneuver the patch to a better position, e.g., a position on the user's skin where a stronger pulse can be detected. This eliminates the need to remove and reattach the adhesive portion from the user's skin.

The present invention also provides a method of forming a medical pulse sensing patch. The method includes the step of forming an opening in a medial portion of a main body that has an upper surface and a lower adhesive surface. The method still further includes the step of positioning a pulse sensor for sensing a pulse within the opening of the main body. The method still further advantageously includes positioning a housing having upper and lower portions to surround the pulse sensor.

This method of forming the medical pulse sensing patch advantageously seals internal components within the housing to protect them from elements that cause rapid deterioration. The method of forming the medical pulse sensing patch is advantageously inexpensive to manufacture and distribute.

The present invention also advantageously provides a method of using a medical pulse sensing patch. The method preferably includes the step of removing the medical pulse sensing patch from a sterile package. The sterile package advantageously insures the caregiver or user that the patch will not be contaminated before it is used to monitor a pulse. The method also advantageously includes positioning the medical pulse sensing patch to overlie and abuttingly contact skin and activating the medical pulse sensing patch by removing a lubricant cover positioned adjacent a lower surface of the medical pulse sensing patch. The step of activating the medical pulse sensing patch advantageously allows the patch to be in a "sleep mode" when not in use. This advantageously allows the medical pulse sensing patch to last longer, thereby reducing waste of patches. This method of using the medical pulse sensing patch also advantageously provides an easy and inexpensive way for caregivers to monitor patients. The method also allows caregivers or users of the medical pulse sensing patch to locate a pulse, apply the patch and monitor the pulse with ease. The step of locating the pulse advantageously allows the caregiver or user the opportunity to move the patch along portions of the skin to find a stronger pulse before adhesively attaching the pulse sensing patch to the skin. The ease and speed with which caregivers can use the medical pulse sensing patch to monitor patients allows better utilization of time so as to provide higher levels of care to more patients.

BRIEF DESCRIPTION OF THE DRAWINGS

Some of the features, advantages, and benefits of the present invention having been stated, others will become apparent as the description proceeds when taken in conjunction with the accompanying drawings in which.

DETAILED DESCRIPTION OF PREFERRED EMBODIMENTS

The present invention will now be described more fully hereinafter with reference to the accompanying drawings which illustrate preferred embodiments of the invention. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout, the prime notation, if used, indicates similar elements in alternative embodiments.

Figure 1:
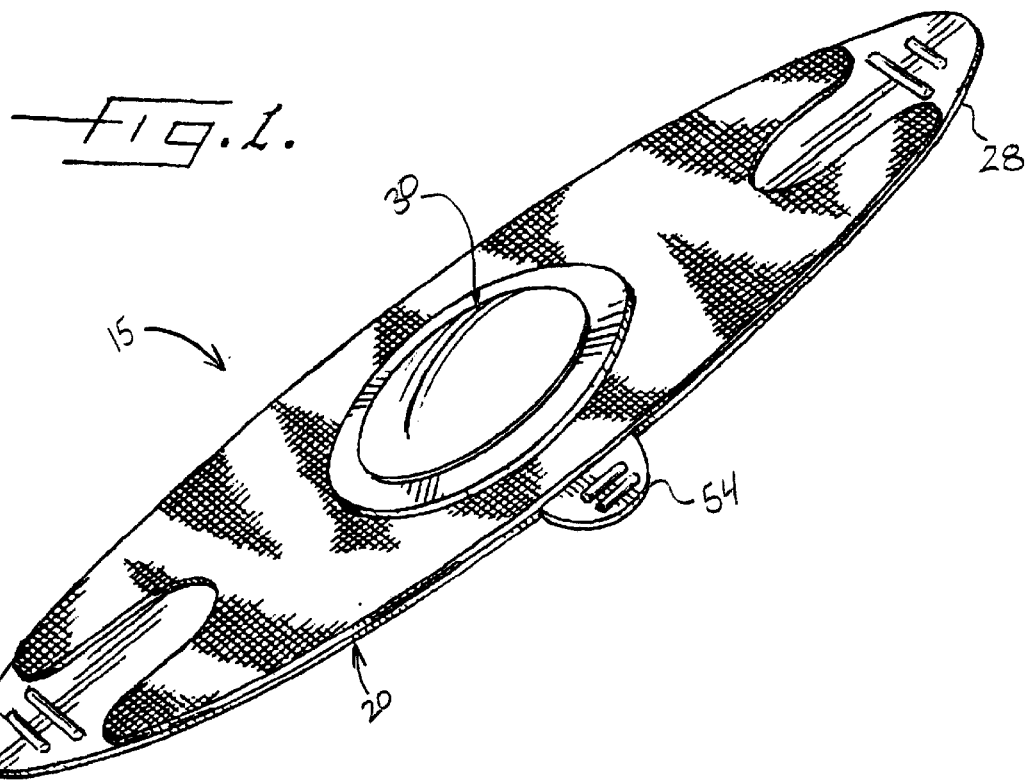
FIG. 1 is a perspective view of a pulse sensing patch according to an embodiment of the present invention.
Figure 2:
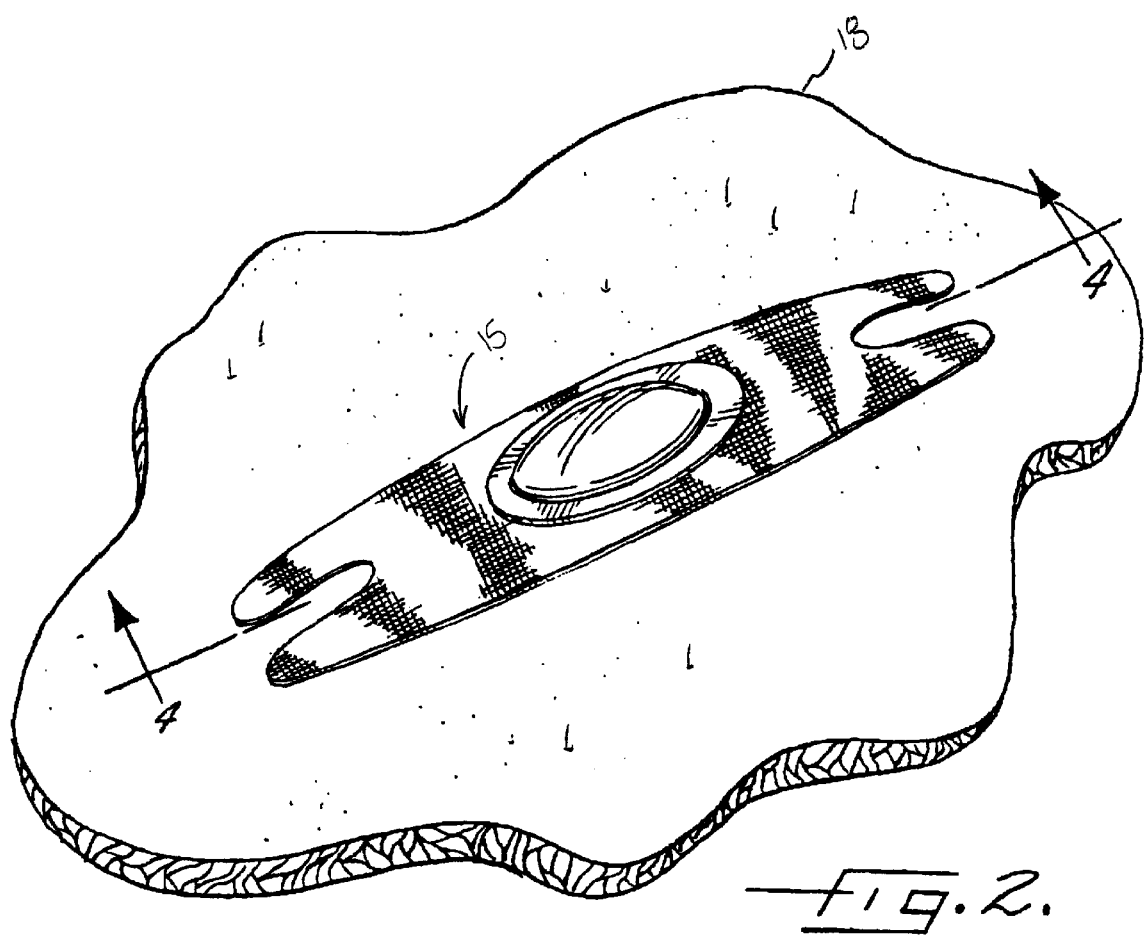
FIG. 2 is an environmental perspective view of a pulse sensing patch positioned to overlie and contact a user's skin according to an embodiment of the present invention.
Figure 4:
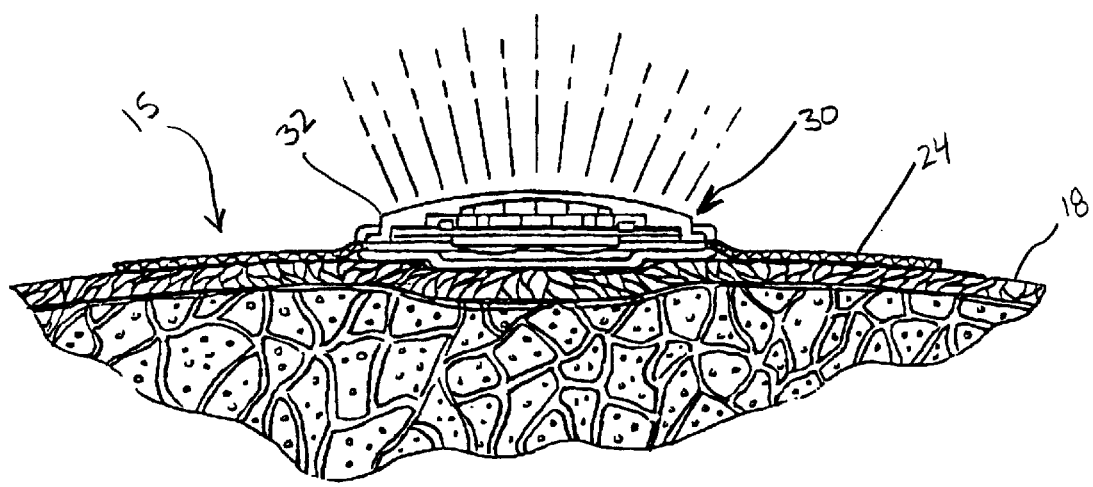
FIG. 4 is a sectional view of a medical pulse sensing patch positioned on a user's skin taken along line 4—4 of FIG. 2 according to an embodiment of the present invention.

As illustrated in FIG. 1, the pulse sensing patch 15 has a main body 20 which can advantageously have an elongate shape, or any shape that provides contact area between the medical pulse sensing patch 15 and skin 18. An elongate shape advantageously provides greater surface area for the medical pulse sensing patch 15 to contact the skin 18, thereby providing a more secure skin or epidermis connection of the patch 15 to the skin 18 (See FIGS. 2 and 4). The main body 20 preferably includes an upper surface 24, a lower adhesive surface 26, and an opening 22 preferably positioned in a medial portion of the main body 20. The upper surface 24 of the main body 20 can be a fabric type of material, such as a bandage, gauze material, or a flexible fabric strap.

The pulse sensing patch 15 also preferably includes a housing 30 having upper 32 and lower 34 portions positioned to surround the opening 22 in the medial portion of the main body 20. The housing 30 can advantageously be provided by a plastic material, for example, or another translucent material through which illumination can be visualized. The upper portion 32 of the housing 30 is positioned to contact the upper surface 24 of the main body 20. The lower portion 34 of the housing 30 is positioned to contact the lower surface 26 of the main body 20. The combination of the upper 32 and lower 34 portions of the housing 30 secure portions of the main body 20, thereby maintaining the position of the opening 22 in the medial portion of the main body 20 with the respect to the housing 30. The medial pulse sensing patch 15 also preferably includes a housing seal 36 that is positioned to overlie and contact the upper portion 32 of the housing 30. The housing seal 36 advantageously seals the housing 30 so as to protect internal components from elements that cause rapid deterioration. The housing seal 36 has a shape substantially similar to the shape of the opening 22 in the medial portion of the main body 20. The housing seal 36 can be provided by a plastic or rubber material, for example, or any other type of material having sealing properties, i.e., paste, gel, rubber, elastomer material, or even tape.

The upper portion 32 of the housing 30 can advantageously be provided by a translucent plastic cover having a faceted interior portion. The faceted interior portion of the upper portion 32 of the housing 30 can advantageously be provided by an opaque lens. The faceted interior portion advantageously enhances illumination of the medical pulse sensing patch 15. The faceted interior portion of the housing 30 can further advantageously direct illumination in a particular direction. For example, in the health care field, a caregiver may desire illumination to be directed away from the patient, so that the patient will not be disturbed when resting. The caregiver may also advantageously direct illumination towards an entrance to a room, for example, allowing the caregiver to monitor the pulse from a distance. The user of the patch 15 may also desire privacy when monitoring their pulse and therefore can advantageously direct the illumination to be only visible to the user.

Figure 5:
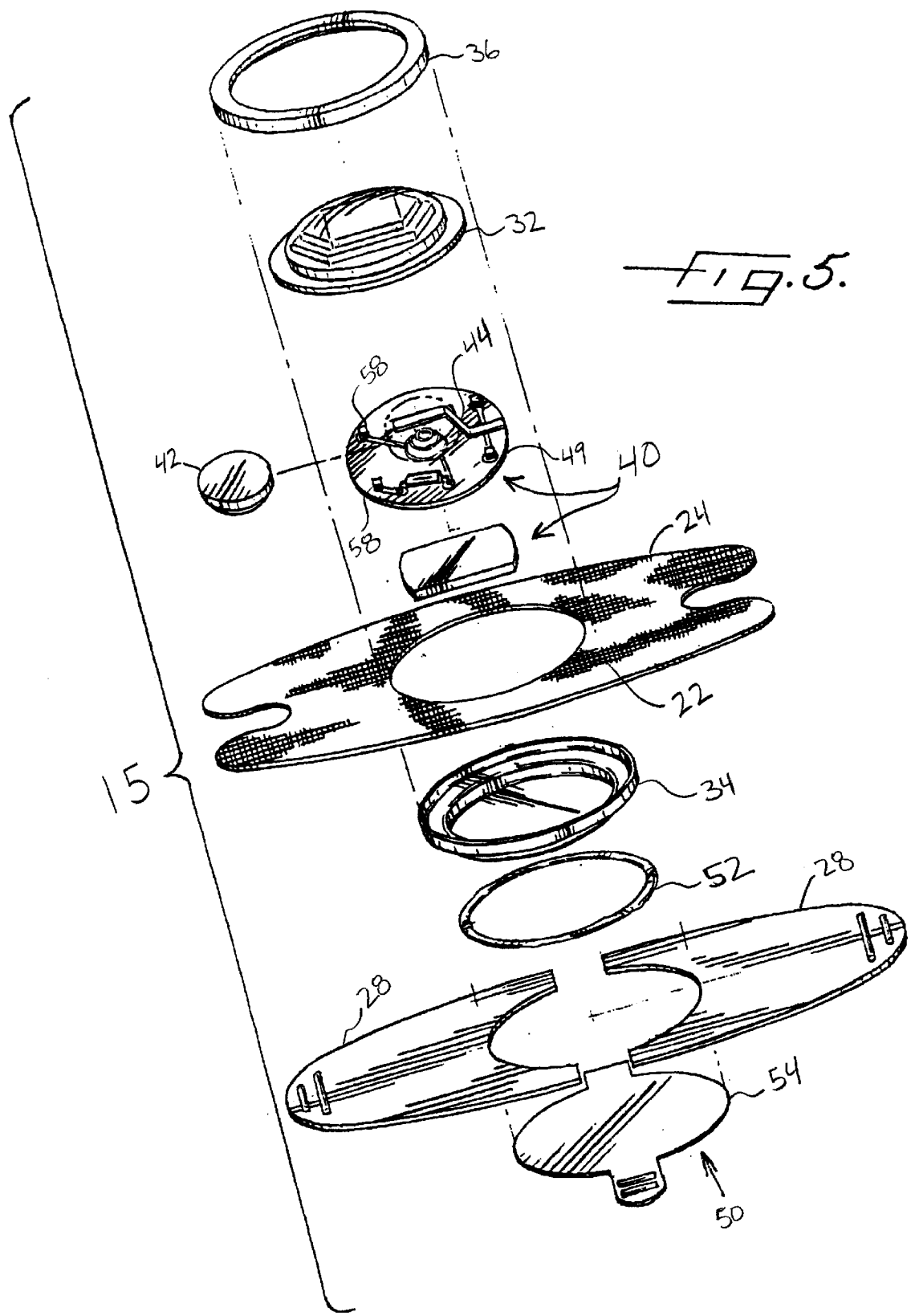
FIG. 5 is an exploded perspective view of a medical pulse sensing patch showing components of a pulse sensing patch according to an embodiment of the present invention.

The medical pulse sensing patch 15 also includes pulse sensing means 40, for sensing a pulse and at least one visual indicator 58 in communication with the pulse sensing means. The visual indicator 58 is advantageously positioned within the housing 30 to be protected from contaminating elements. The visual indicator 58 can advantageously be provided by a light emitting diode, for example, or another source of illumination such as vacuum flourescent color liquid crystal, electro-luminescence, or incandescent illumination. The pulse sensing means 40 preferably includes a pulse sensor, a microprocessor, a transmitter, and a receiver. The transmitter can, for example, be an infrared diode and the receiver, for example, can be an infrared photo-resister. The pulse sensing means 40 is also positioned within the housing 30, as best illustrated in FIG. 5, to be protected from contaminating elements. The pulse sensor can, for example, advantageously be provided by an infrared signal. The pulse sensing means 40 can advantageously include a microcontroller or other processing circuitry, preferably provided by a microprocessor with software, as understood by those skilled in the art. The microprocessor is positioned on a main printed circuit board 49. The microprocessor differentiates between a pulse and artifact noise, as understood by those skilled in the art. The microprocessor also advantageously qualifies the strength of the pulse. The software, for example, recognizes the different stages of use of the pulse sensing patch 15 and converts the recognized stages to a visually recognizable pattern. For example, the pulse sensor emits an infrared signal through the lower portion 34 of the housing 30 to the skin 18 of the user.

The housing 30 advantageously increases the durability of the patch 15 by providing protection to sensitive internal components from elements that can cause deterioration. The pulse sensor is preferably positioned to overlie the lower portion 34 of the housing and can also be positioned to underlie the visual indicator 58. The transmitter of the pulse sensing means 40 emits a signal through the lower portion 34 of the housing 30 to the skin 18. The receiver of the pulse sensing means 40 receives the signal transmitted back from the skin 18 through the lower portion 34 of the housing 30. The microprocessor of the pulse sensing means 40 receives the signal from the receiver, converts the signal, and transmits a signal to the visual indicator 58 as understood by those skilled in the art.

The medical pulse sensing patch 15 preferably includes a lubricant 52 positioned adjacent an exterior surface of the lower portion 34 of the housing 30. The lubricant 52 preferably has a shape that is substantially similar to the opening 22 in the medial portion of the main body 20. The lubricant 52 can advantageously be provided by a surgical gel in a preferred embodiment. The lubricant 52 can also be provided by any other material that can decrease friction between the medical pulse sensing patch 15 and the skin 18. The lubricant 52 advantageously allows a caregiver to maneuver the medical pulse sensing patch 15 along the skin 18 to locate a pulse or a stronger pulse signal before positioning the lower adhesive surface 26 to adhesively contact the skin 18. The lubricant 52 advantageously provides temporary adhesion between the pulse sensing patch 15 and the caregiver as a pulse is being located. The lubricant 52 also advantageously provides temporary adhesion of the pulse patch 15 to the patient's skin 18 until the lower adhesive surface can be secured to the patient's skin 18.

Figure 3:
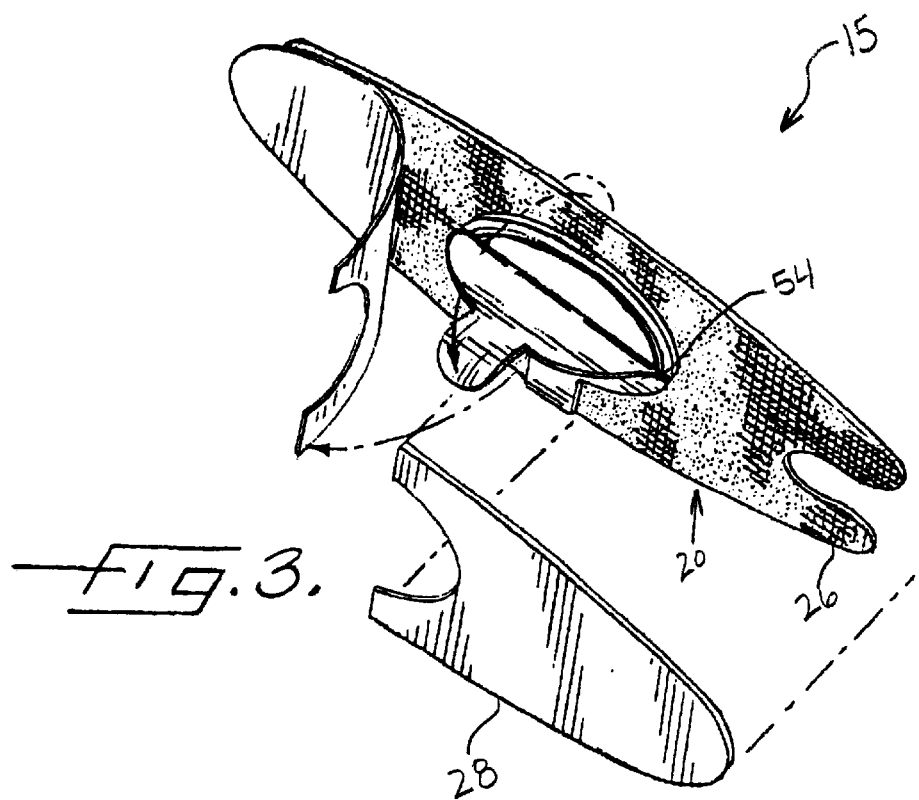
FIG. 3 is an exploded bottom perspective view of a medical pulse sensing patch showing a lubricant cover and adhesive cover strips according to an embodiment of the present invention.

The medical pulse sensing patch 15 advantageously includes pulse sensor activating means 50. The pulse sensor activating means 50 is preferably provided by a lubricant cover 54 as best illustrated in FIG. 3. The lubricant cover 54 is positioned to overlie and abuttingly contact the lubricant 52. When the lubricant cover 54 is removed, the pulse sensing patch 15 is activated. When the patch is activated the visual indicator 58 illuminates to thereby inform the user that the patch 15 has been activated. The lubricant cover 54 can advantageously include a conductive portion. The conductive portion completes a circuit with the pulse sensor. Once the lubricant cover 54 is removed, the circuit between the pulse sensor and the lubricant cover is broken and the pulse sensing patch 15 is activated. When the pulse sensing patch 15 is activated, the infrared signal is emitted from the transmitter. The lubricant cover 54 can also advantageously constrict the infrared signal emitted from the transmitter. When the lubricant cover 54 is removed, the software recognizes that the infrared signal is no longer constricted and the pulse patch 15 is activated. When the lubricant cover 54 is positioned to overlie and abuttingly contact the lubricant 52, the pulse sensing patch 15 is inactive, i.e., in a sleep mode. The pulse sensing patch 15 is not activated until the lubricant cover 54 is removed. This advantageously conserves energy and provides the medical pulse sensing patch 15 with an extended life.

As illustrated in FIG. 3, the medical pulse sensing patch 15 also includes an adhesive surface cover 28. The adhesive surface cover 28 preferably has a shape substantially similar to the main body 20. The adhesive surface cover 28 can advantageously be provided by a plurality of flexible plastic strips positioned to underlie and abuttingly contact the lower adhesive surface 26 of the main body. The adhesive surface cover 28 can also be provided by any type of material that can detachably connect to the lower adhesive surface 26 of the main body 20, such as treated paper, plastic, rubber or a laminated material. The flexible plastic strips advantageously protect the lower adhesive surface 26 until an adhesive connection to the skin 18 is required.

The medical pulse sensing patch 15 can still further include a plurality of visual indicators 58 that can be positioned to overlie the pulse sensing means 40. More specifically, the visual indicators 58 are positioned to overlie and contact the main printed circuit board 49. A plurality of visual indicators 58 advantageously provide more brilliant illumination. Each of the plurality of visual indicators 58 can advantageously emit light or glow any one of a plurality of different colors. Each of the plurality of visual indicators 58 emits a first color, for example red, when the lubricant cover 54 is removed to thereby indicate that the medical pulse sensing patch 15 has been activated. This advantageously allows a caregiver to immediately recognize that the medical pulse sensing patch 15 is activated and is ready for application to the skin 18. Each of the plurality of visual indicators 58 then emits another of a plurality of different colors, for example yellow, when the pulse is initially located. The plurality of visual indicators 58 will continue to glow yellow, for example, if there is only a weak detection of the pulse. Each of the plurality of visual indicators 58 can also emit yet another of a plurality of colors, for example green, when the pulse is located and confirmed by the software. When the medical pulse sensing patch 15 is positioned over the pulse and the lower adhesive surface 26 is applied to the skin 18, thereby adhesively connecting the patch 15 to the skin 18, each of the plurality of visual indicators 58 provides a predetermined or preselected indication pattern that is substantially similar to the timing of the pulse. Each of the plurality of light emitting diodes, for example, will blink one time for every time that a heartbeat is detected by the pulse sensing means 40. The plurality of visual indicators 58 blink in unison so that the plurality of visual indicators 58 blinking together in unison provide a more enhanced visual indication of the pulse.

The medical pulse sensing patch 15 also preferably includes a portable and compact power source that is positioned adjacent the pulse sensing means 40 and visual indicators 58. The power source can advantageously be provided by a combination of a small and inexpensive battery 42, e.g., a watch battery, and a battery clip 44 or battery holder. The battery clip 44 is positioned to electrically contact the battery 42 and secure it in place within the housing 30. When the pulse sensor activating means 50, provided by the lubricant cover 54, is positioned over the lubricant 52, power does not flow to the components of the medical pulse sensing patch 15. Therefore, the power available from the battery 42 is conserved until the lubricant cover 54 is removed and the medical pulse sensing patch 15 is activated. This advantageously allows the power source to last for an extended period of time.

Figure 6:
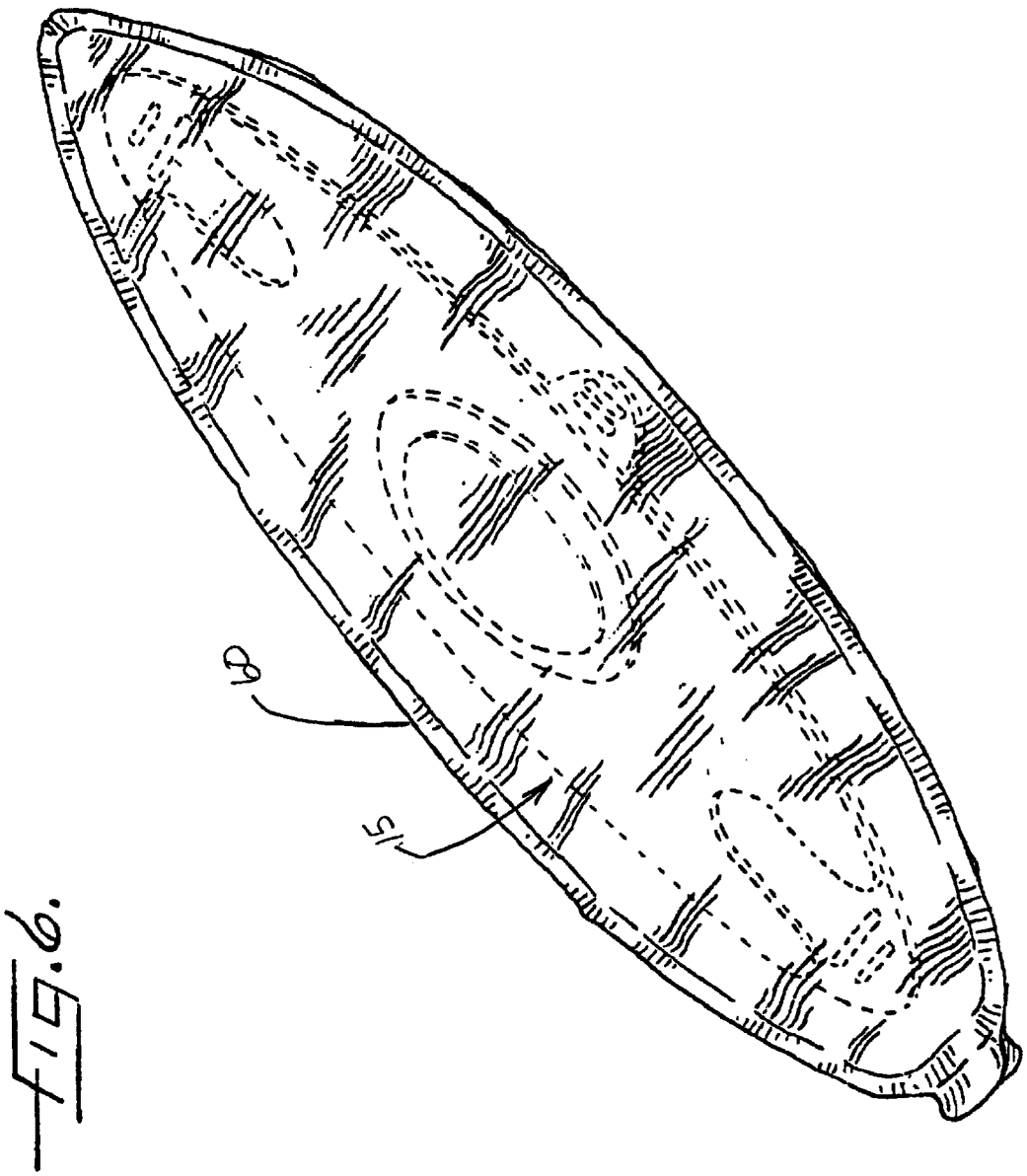
FIG. 6 is a perspective view of a pulse sensing patch having a sterile medical pulse sensing patch wrapper according to an embodiment of the present invention.

The medical pulse sensing patch 15 still further includes a sterile package 60, as best illustrated in FIG. 6. The sterile package 60 advantageously insures that the medical pulse sensing patch 15 is sterile and safe before use. In a preferred embodiment, the sterile package 60 can advantageously be a strong, flexible, paper package having a shape substantially similar to the main body 20 of the medical pulse sensing patch 15. The sterile package 60 can also be provided by any form of packaging, i.e., plastic vacuum wrap, that can keep the medical pulse sensing patch 15 sterile. The sterile package 60 is preferably sealed along all edge portions of the package to prevent outer contaminants from entering the package 60. The sterile package 60 also advantageously includes a portion that can be easily opened by the user or caregiver with minimal effort. This is advantageous when used by weaker patients that may have difficulty opening packages with strong seals. The sterile package 60 also greatly decreases the possibility of spreading an infection by keeping the medical pulse sensing patch 15 sterile. This is especially advantageous when the medical pulse sensing patch 15 is to be used for patients that have weak immune systems.

The medical pulse sensing patch 15 advantageously allows caregivers to monitor pulse rates of patients without actually taking the time needed to physically locate and count the pulse rate. It also advantageously allows users to monitor their own pulses without the aid of a caregiver. The interior components of the medical pulse sensing patch 15 are advantageously sealed within the housing 30 and protected from contamination by exterior elements. This advantageously provides a medical pulse sensing patch 15 that is suited for extended use.

The medical pulse sensing patch 15 is advantageously inexpensive to manufacture and safe to use. This allows for the patch 15 to be readily available in hospitals, easing a caregiver's burden of caring for several patients at one time. The medical pulse sensing patch 15 can also be distributed to patients for their use at home, sports, or entertainment locations or venues or even be distributed to children as an educational tool or jewelry. Children can advantageously safely apply the medical pulse sensing patch 15 to a portion of their skin to monitor their own pulses, and learn about the medical significance of blood flow in their bodies. This can advantageously increase a child's desire to learn more about the medical field. The patch 15 can also advantageously be used as jewelry by children, or may be worn in entertainment venues, such as night clubs and concerts, for example.

The present invention provides a method of forming a pulse sensing patch 15. The method includes the step of forming an opening 22 in a medial portion of a main body 20, the main body 20 having an upper surface 24 and a lower adhesive surface 26. The method also includes the step of positioning pulse sensing means 40 for sensing a pulse within the opening 22 of the main body 20. The method of forming the pulse sensing patch 15 still further includes the step of positioning a housing 30 having upper 32 and lower 34 portions to surround the pulse sensing means 40. This method of forming the medical pulse sensing patch 15 also advantageously includes positioning at least one visual indicator 58 to overlie the pulse sensing means 40 within the housing 30. The method still further advantageously includes sealing the housing 30 by positioning a housing seal 36 adjacent an upper portion 32 of the housing 30. Sealing the medical pulse sensing patch 15 provides protection to internal components from external contamination elements.

The method of forming the medical pulse sensing patch 15 also advantageously includes positioning a lubricant 52, having substantially the same shape as the opening 22, in the main body 20 to abuttingly contact the lower portion 34 of the housing 30. Positioning a lubricant 52 adjacent the lower portion 34 of the housing 30 advantageously allows a caregiver or user to maneuver the medical pulse sensing patch 15 along skin 18 until a strong pulse is located. This also advantageously temporarily adheres the pulse sensing patch 15 to the back of the caregiver's hand as the caregiver locates the pulse.

The method still further includes positioning an adhesive cover 28 to overlie and abuttingly contact the lower adhesive surface 26 of the main body 20. The adhesive cover 28 has substantially the same shape as the main body 20. Positioning the adhesive covers 28 to abuttingly contact the lower adhesive surface 26 advantageously protects the lower adhesive portion 26 of the medical pulsating patch 15 from external contaminating elements. The method also advantageously includes positioning the main body 20 and interior components within a sterile package 60 and sealing the sterile package 60. This advantageously provides a medical pulse sensing patch 15 that is sterile and free from contaminates that may cause infection to patients with weak immune systems.

Figure 7:
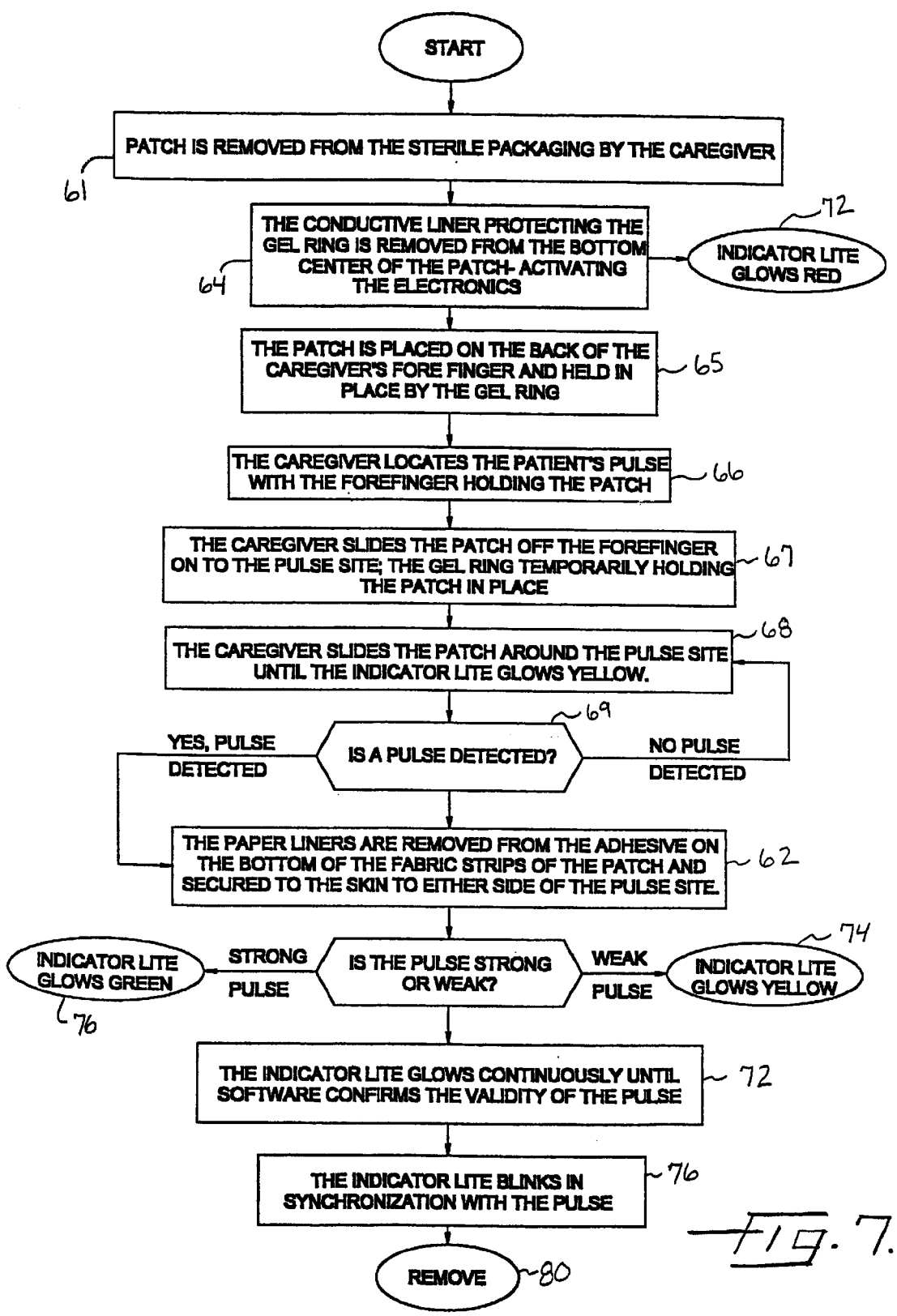
FIG. 7 is a flowchart showing the steps for use of a medical pulse sensing patch according to an embodiment of the present invention.

As illustrated in a flowchart in FIG. 7, the present invention also advantageously provides a method of using a medical pulse sensing patch 15. The method preferably includes removing 61 the medical pulse sensing patch 15 from a sterile package 60, activating 64 the medical pulse sensing patch 15 by removing a lubricant cover 54 positioned to underlie and detachably contact a lubricant 52 positioned along a lower surface of a lower portion 34 of a housing 30, and positioning 62 the medical pulse sensing patch 15 to overlie and abuttingly contact skin 18.

The method further includes positioning 65 the medical pulse sensing patch 15 to slidably contact a finger, for example, the caregiver's finger, and locating a pulse 66 using the finger. The method still further includes sliding 67 the patch 15 over the caregiver's finger and positioning the patch 15 over the located pulse. The method also advantageously includes moving 68 the medical pulse sensing patch 15 along portions of the skin 18 to better locate the pulse. The method further advantageously includes exposing 62 a lower adhesive surface 26 of the patch 15 by detaching an adhesive cover 28 from the lower adhesive surface 26. The method also includes the step of securing 62 the medical pulse sensing patch 15 to the skin 18 by contacting the lower adhesive portion 26 with portions of the skin 18. Once the pulse is located by maneuvering 68 the medical pulse sensing patch 15 along the skin 18, the lower adhesive portion 26 of the patch 15 is positioned to make contact 62 with portions of the skin 18, thereby adhesively connecting the pulse patch 15 to the user's skin 18.

The method of using the medical pulse sensing patch 15 also includes the step of detecting 69 and transmitting a pulse with a pulse sensing means 40. More particularly, this includes transmitting a pulse signal from a pulse sensor to a microprocessor. The method further includes converting the pulse signal and transmitting it from the microprocessor to a visual indicator 58.

The method of using the medical pulse sensing patch 15 still further includes the step of visualizing 72 one of a plurality of indication patterns from the visual indicator 58, for example, a light emitting diode, when the medical pulse sensing patch 15 is activated. The visual indicator 58 can advantageously emit any one of a plurality of colors, for example red, when the lubricant cover 54 is removed, thereby activating the patch 15. The method of using the medical pulse sensing patch 15 also advantageously includes the step of visualizing another of a plurality of indication patterns 74, for example a yellow light, when the pulse is located, and another pattern 76, such as emitting a green light, if the sensor recognizes a stronger pulse. The method still further includes the step of visualizing another one of a plurality of predetermined indication patterns 76, for example, a blinking green light, having timing substantially similar to the pulse. The visual indicator 58, for example, can blink once for every heartbeat detected by the pulse sensing means 40.

The method of using the medical pulse sensing patch 15 also advantageously includes removing 80 the medical pulse sensing patch 15 from the skin 18 when monitoring of the pulse has been completed. Removing 80 the medical pulse sensing patch 15 is easily accomplished by lifting the lower adhesive surface portion 26 of the main body 20 thereby detaching the medical pulse sensing patch 15 from the skin 18.

The method of using the medical pulse sensing patch 15 advantageously allows caregivers to monitor the pulse of patients rapidly and with great ease. This also advantageously allows caregivers to provide a higher level of care to a greater number of patients. The method of using the medical pulse sensing patch 15 allows the caregiver to quickly locate the user's pulse, apply the medical pulse sensing patch 15 and move to another task, such as administering medication or making the patient more comfortable. The caregiver no longer has to use valuable time to physically monitor the pulse. The method of using the medical pulse sensing patch 15 also advantageously allows persons that do not have medical training to monitor their own pulse. A person that has a heart condition, for example, can monitor their heart rate without the assistance of a caregiver. The method of using the medical pulse sensing patch 15 also advantageously provides persons not able to afford the services of a caregiver an opportunity to monitor their pulse without incurring exorbitant medical bills that can accumulate from regular visits to a medical professional.

In the drawings and specification, there have been disclosed a typical preferred embodiment of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

What is claimed is:

1. A medical pulse sensing patch comprising:
    a main body having an upper surface, a lower adhesive surface and an opening positioned in a medial portion of said main body;
    a housing having upper and lower portions positioned to surround the opening in the medial portion of the main body, the upper portion positioned to contact the upper surface of the main body, and the lower portion positioned to over lap and contact the lower surface of the main body;
    pulse sensing means positioned within said housing for sensing a pulse; and
    a plurality of visual indicators positioned to overlie the pulse sensing means and also positioned within the housing for displaying a visually recognizable pattern of the pulse.

2. The medical pulse sensing patch as defined in claim 1, further comprising a lubricant positioned to abuttingly contact a lower surface of the lower portion of the housing to thereby provide lubrication between the medical pulse sensing patch and skin.

3. The medical pulse sensing patch as defined in claim 2, wherein the lubricant further comprises a shape substantially similar to the opening in the medial portion of the main body.

4. The medical pulse sensing patch as defined in claim 3, further comprising pulse sensor activating means for activating the pulse sensing means.

5. The medical pulse sensing patch as defined in claim 4, wherein the pulse sensor activating means further comprises a lubricant cover positioned to detachably contact the lubricant.

6. The medical pulse sensing patch as defined in claim 5, wherein the lubricant cover further comprises a shape substantially similar to the shape of the lubricant.

7. The medical pulse sensing patch as defined in claim 6, wherein the pulse sensing means is activated when the lubricant cover is detached from the lubricant positioned adjacent the lower portion of the housing.

8. The medical pulse sensing patch as defined in claim 7, wherein the pulse sensing means further comprises a pulse sensor and a microprocessor positioned to overlie said pulse sensor for sensing, converting, and transmitting the pulse to the plurality of visual indicators.

9. The medical pulse sensing patch as defined in claim 8, wherein the pulse sensor further comprises a transmitter and a receiver for transmitting a pulse signal from the pulse sensing means through the lower portion of the housing to the skin and for receiving said signal transmitted back from the skin through the lower portion of the housing to the pulse sensor.

10. The medical pulse sensing patch as defined in claim 9, wherein the microprocessor receives a signal from the receiver, converts said signal and transmits said signal to the plurality of visual indicators.

11. The medical pulse sensing patch as defined in claim 10, wherein each of the plurality of visual indicators further comprises a plurality of colors for identifying different stages of use of the medical pulse sensing patch.

12. The medical pulse sensing patch as defined in claim 11, wherein each of the plurality of visual indicators glows a first color when the lubricant cover is detached from the lubricant to thereby indicate that the medical pulse sensing patch is active.

13. The medical pulse sensing patch as defined in claim 12, wherein each of the plurality of visual indicators glows a second color when the pulse is identified by the pulse sensing means.

14. The medical pulse sensing patch as defined in claim 13, wherein each of the plurality of visual indicators further includes a predetermined indication pattern to thereby identify timing of the pulse.

15. The medical pulse sensing patch as defined in claim 14, wherein the upper portion of the housing further comprises a translucent cover having a faceted interior lens portion for enhancing emissions of light from the plurality of visual indicators.

16. The medical pulse sensing patch as defined in claim 15, further comprising a housing seal positioned to overlie and contact the upper portion of the housing to thereby seal said housing.

17. The medical pulse sensing patch as defined in claim 16, further comprising a plurality of flexible adhesive covers having a shape substantially similar to the main body and positioned adjacent the lower adhesive surface of said main body.

18. The medical pulse sensing patch as defined in claim 17, further comprising a sterile package positioned to cover and enclose the medical pulse sensing patch.

19. A medical pulse sensing patch comprising:
    a main body having an upper surface, a lower adhesive surface and an opening positioned in a medial portion of said main body;
    pulse sensing means positioned within a housing for sensing a pulse;
    pulse sensor activating means positioned to underlie the pulse sensing means exterior to the housing for activating the pulse sensing means; and
    at least one visual indicator positioned to overlie the pulse sensing means and also positioned within the housing for displaying a visually recognizable pattern of the pulse.

20. The medical pulse sensing patch as defined in claim 19, wherein the housing further comprises upper and lower portions positioned to surround the opening in the medial portion of the main body and wherein the upper portion of the housing is positioned to contact the upper surface of the main body and the lower portion of the housing is positioned to contact the lower adhesive surface of the main body.

21. The medical pulse sensing patch as defined in claim 20, further comprising a lubricant positioned to abuttingly contact a lower surface of the lower portion of the housing to thereby provide lubrication between the medical pulse sensing patch and skin.

22. The medical pulse sensing patch as defined in claim 21, wherein the lubricant further comprises a shape substantially similar to the opening in the medial portion of the main body.

23. The medical pulse sensing patch as defined in claim 22, wherein the pulse sensor activating means further comprises a lubricant cover positioned to detachably contact the lubricant.

24. The medical pulse sensing patch as defined in claim 23, wherein the lubricant cover further comprises a shape substantially similar to the shape of the lubricant.

25. The medical pulse sensing patch as defined in claim 24, wherein the pulse sensing means is activated when the lubricant cover is detached from the lubricant positioned adjacent the lower portion of the housing.

26. The medical pulse sensing patch as defined in claim 25, wherein the pulse sensing means further comprises a pulse sensor and a microprocessor positioned to overlie said pulse sensor for sensing, converting, and transmitting the pulse to the at least one visual indicator.

27. The medical pulse sensing patch as defined in claim 26, wherein the pulse sensor further comprises a transmitter and a receiver for transmitting a pulse signal from the pulse sensing means through the lower portion of the housing to the skin and for receiving said signal transmitted back from the skin through the lower portion of the housing to the pulse sensor.

28. The medical pulse sensing patch as defined in claim 27, wherein the microprocessor receives a signal from the receiver, converts said signal and transmits said signal to the at least one visual indicator.

29. The medical pulse sensing patch as defined in claim 28, wherein the at least one visual indicator further comprises a plurality of colors for identifying different stages of use of the medical pulse sensing patch.

30. The medical pulse sensing patch as defined in claim 29, wherein each of the plurality of visual indicators glows a first color when the lubricant cover is detached from the lubricant to thereby indicate that the medical pulse sensing patch is active.

31. The medical pulse sensing patch as defined in claim 30, wherein the at least one visual indicator glows a second color when the pulse is identified by the pulse sensing means.

32. The medical pulse sensing patch as defined in claim 31, wherein the at least one visual indicator further includes a predetermined indication pattern to thereby identify a visually recognizable indication of the timing of the pulse.

33. The medical pulse sensing patch as defined in claim 32, wherein the upper portion of the housing further comprises a translucent cover having a faceted interior lens portion for enhancing emissions of light from the plurality of light emitting diodes.

34. The medical pulse sensing patch as defined in claim 33, further comprising a housing seal positioned to overlie and contact the upper portion of the housing to thereby seal said housing.

35. The medical pulse sensing patch as defined in claim 34, further comprising a plurality of flexible plastic strips having a shape substantially similar to the main body and positioned adjacent the lower adhesive surface portion of said main body.

36. The medical pulse sensing patch as defined in claim 35, further comprising a sterile package positioned to cover and enclose the medical pulse sensing patch.

37. A pulse sensing device comprising:

a main body having an upper surface, a lower adhesive surface, and an opening positioned in the main body;

a pulse sensor positioned in the main body and adapted to overlie the skin of a user, the pulse sensor further comprising
a transmitter positioned in the main body for transmitting a signal to the skin of the user; and
a receiver positioned in the main body for receiving the signal returned from the skin of the user;

a microprocessor positioned in the housing for converting the signal received from the skin of the user to a visually-identifiable pattern of a pulse;

a plurality of independent indicators each responsive to the microprocessor and each positioned in the main body to separately indicate the visually identifiable pattern of the pulse and a relative strength of the pulse detected by said pulse sensor; and a compact and portable power source positioned in the main body.

38. The pulse sensing device as defined in claim 37, wherein the power source further comprises a battery and a battery holder positioned to contact and secure said battery.

39. The pulse sensing device as defined in claim 38, wherein the signal transmitted from the transmitter and to the receiver is an infrared signal.

40. The pulse sensing device as defined in claim 39, wherein the microprocessor further comprises software for converting the infrared signal to a visually identifiable pattern.

\* \* \* \* \*